United States Patent [19]

Enge

[11] 4,122,346
[45] Oct. 24, 1978

[54] OPTICAL DEVICES FOR COMPUTED TRANSAXIAL TOMOGRAPHY

[75] Inventor: Harald Anton Enge, Winchester, Mass.

[73] Assignee: High Voltage Engineering Corporation, Burlington, Mass.

[21] Appl. No.: 780,492

[22] Filed: Mar. 23, 1977

[51] Int. Cl.² ............................................. H01J 3/14
[52] U.S. Cl. ............................ 250/398; 250/396 ML
[58] Field of Search ............ 250/398, 396 ML, 445 T; 313/359, 360; 335/210, 213

[56] References Cited

U.S. PATENT DOCUMENTS

| 3,500,269 | 3/1970 | Katagiri et al. ............ 250/396 ML |
| 3,660,658 | 5/1972 | Lebontet et al. .................... 250/398 |
| 3,671,895 | 6/1972 | Aucouturier et al. ....... 250/396 ML |
| 3,818,394 | 6/1974 | Katagiri et al. ............ 250/396 ML |

Primary Examiner—Alfred E. Smith
Assistant Examiner—B. C. Anderson
Attorney, Agent, or Firm—Russell & Nields

[57] ABSTRACT

Various optical devices for use with circular-scanning techniques in computed transaxial tomography are disclosed. In essence such devices produce a rotating dipole field so as simultaneously to provide a circular scan and to focus the charged particle beam on the circular target.

6 Claims, 6 Drawing Figures

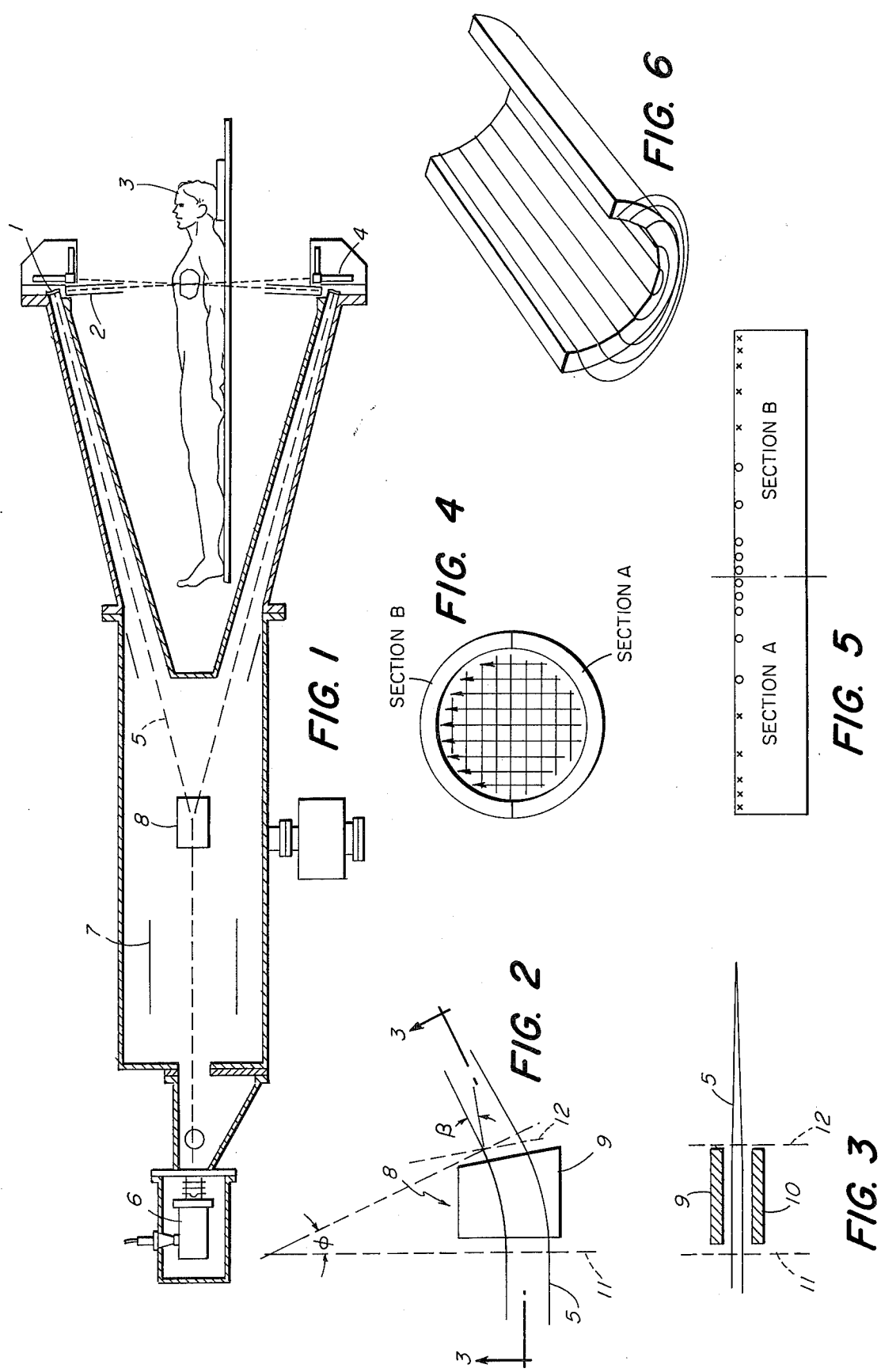

OPTICAL DEVICES FOR COMPUTED TRANSAXIAL TOMOGRAPHY

BACKGROUND OF THE INVENTION

Computed transaxial tomography techniques have recently been disclosed and developed. In particular there has recently been disclosed and claimed apparatus for producing circularly scanned charged-particles which, when striking a target, produce a rotating x-ray beam suitable for use in computed transaxial tomography. Such devices can operate using any one of a variety of beam scanning apparatus which are well known in connection with cathode-ray oscilloscopes, radar, etc. However, a major use of circularly scanned beams is for the production of fast x-ray scans, as in the case of taking x-ray "pictures" of moving objects, such as a human heart. Such fast x-ray scans require a rapidly scanned charged-particle beam, and if such a beam is to produce x-rays of adequate intensity, high beam currents must be employed. Because of space charge effects and other phenomena, the need for high beam currents automatically requires that the beam have a relatively large cross-section at the place where it is deflected. The beam must then be focused so as to converge strongly at the target in at least one dimension, so as to provide high resolution. The deflection and focusing of such high-current, large-cross-section beams requires a radically different approach from those taught by the prior art.

SUMMARY OF THE INVENTION

In one embodiment of the invention the objectives of high beam current and optimum focus in a circularly scanned x-ray device are accomplished through the use of a rotating dipole field. While such a field can be produced by mechanically rotating a simple dipole (i.e. a beam-deflecting magnet), in a preferred embodiment of the invention the rotating field is produced electrically using stationary coils.

DETAILED DESCRIPTION OF THE PREFERRED EMBODIMENTS

The invention may best be understood from the following detailed description thereof, having reference to the accompanying drawings in which:

FIG. 1 is a vertical central section showing somewhat schematically a circularly scanned x-ray device with which the rotating dipole field of the invention may be employed;

FIG. 2 is a diagrammatic view in longitudinal central section of one of a pair of pole pieces which may be rotated mechanically in accordance with the invention;

FIG. 3 is a section along the line 3—3 of FIG. 2;

FIG. 4 is a transverse section taken through coils embodying a second form of the invention;

FIG. 5 is a view similar to that of FIG. 4 except that the coils and magnetic material are folded out in a straight line from their actual annular position so as to show the arrangement of the windings;

FIG. 6 is a perspective view of the coils of FIGS. 4 and 5.

Referring to the drawings and first to FIG. 1 thereof, the apparatus therein shown is adapted to produce a circularly scanned x-ray beam. The x-rays are produced at a circular target 1, and x-ray collimators 2 collimate the emergent x-rays so that they are directed towards a patient 3 supported near the axis of the annular target 1. An annulus of detectors 4 is arranged as close as possible to the annular target 1. The output of the detectors 4 is delivered in a well-known manner to computer apparatus which provides the desired x-ray picture of a cross-sectional slice of the patient's body. The x-rays are produced at the target 1 by bombarding the same with a charged-particle beam 5. The charged-particle beam 5 is produced in a conventional particle accelerator 6 and is directed into a focusing ion lens arrangement 7 which may consist of quadrupoles or a solenoid. The charged-particle beam 5 is circularly scanned about the annular target 1 and simultaneously focused thereat by a deflector-focuser 8 constructed in accordance with the invention. The simplest form of deflector focuser 8 will now be described.

Referromg now to FIGS. 2 and 3, the deflector focuser therein shown comprises a simple pair of magnetic poles flanking the beam 5. One such magnetic pole is shown at 9 in FIG. 2, and the pair of pole pieces 9, 10, is shown in FIG. 3. As is well known, a uniform magnetic field such as that produced by pole pieces 9, 10 deflects a charged-particle beam into a circular path having a radius of curvature R. Because of the fringing fields, the effective length of the magnet is somewhat larger than the physical length of the pole pieces. Thus, in FIGS. 2 and 3 the incident effective field boundary is shown at 11 and the exit effective field boundary is shown at 12. Each charged particle in the beam 5 approaches the entrance effective boundary 11 in a rectilinear path, travels between boundaries 11 and 12 in a circular path of radius R, and emerges from the exit effective boundary 12 in a rectilinear path which is at an angle $\phi$ with respect to the incident path. The field strength and size of the pole pieces 9, 10 are so chosen that the angle $\phi$ will direct the charged-particle beam onto the annular target 1. The pole pieces 9, 10 are connected, in accordance with well-known techniques, by a yoke (not shown) and are energized by suitable coils (not shown). The charged-particle beam is then scanned over the target by simple mechanical rotation of the pair of pole pieces 9, 10. It will be appreciated that since both the size of the pole pieces and the strength of the magnetic field are variable parameters for the designer, the angle $\phi$ may be fixed and yet the radius of curvature R may still be varied if desired. This now permits adjustments in the design stage of the focusing of the charged-particle beam 5 in addition to deflection thereof.

The exit-fringing field of a simple dipole as shown in FIGS. 2 and 3 gives focusing in the transverse plane, and the focal length is a function of the exit angle $\beta$, which is the angle between the normal to the exit effective boundary 12 and the emergent ray. In general, $\beta$ should not be less than $\phi/2$, and the strength and dimensions of the magnetic field are chosen such that the focusing action for azimuthal focusing is as close to the target as possible. In the case of a beam which crosses the incident effective field boundary as parallel trajectories, if $\beta = \phi$ the exit fringing field does not produce any focusing in the median plane and the focusing action in the transverse plane has a focal length equal to or slightly greater than $R/\tan \beta$. In accordance with usual terminology, the median plane is the plane of the drawing in FIG. 2 and is the plane perpendicular to the drawing which lies midway between the pole pieces 9 and 10 of FIG. 3. Again in accordance with the usual terminology, the transverse "plane" is the plane perpendicular to the plane of the drawing in FIG. 2 which is aligned with the axis of the charged-particle beam. Thus the transverse plane is perpendicular to the plane of the drawing of FIG. 2, and lies in the plane of the drawing of FIG. 3. In a representative circularly scanned device such as that shown in FIG. 1, the angle φ is 30°, and if the pole pieces 9, 10 are now adjusted with respect to size and strength of magnetic field so as to produce a radius of curvature R of 100 centimeters, and if one assumes a parallel beam and an exit angle β = φ, the resultant focal length f is approximately 200 centimeters, which is appropriate for a circularly-scanned x-ray device of the type shown in FIG. 1.

In circularly scanned tomography, it is important that the charged particle beam be focused in the azimuthal direction. The azimuthal direction corresponds to the circumferential dimension of the annular target. If the spot on the target is narrow in this direction, the x-rays fan out in the planar slice of the object being "photographed" from a "point" source. The focus of the charged particle beam in the radial or "spot length" direction is not critical, and the spot length can be reduced by altering the target angle so that it is more nearly perpendicular to the axis of the beam. However, under certain circumstances it may be desirable to provide focusing in the radial or "spot length" direction as well as in the azimuthal direction.

Most of the focusing effect is provided by the solenoid or other focusing device, which focuses in both planes. The solenoid or other focusing device may thus provide adequate focusing in the radial direction. However, if additional focusing in the radial direction is desired, the deflector-focuser may be adjusted to provide such focusing by arranging the orientation of the exit effective boundary 12 so that it is not parallel to the entrance effective boundary 11, but at an angle thereto so that β is a little less than φ, as shown in FIG. 2.

The device producing azimuthal focusing should be as close to the target as possible, in order to produce the smallest possible magnification in the azimuthal direction. It is possible that in the radial direction one may not want a true image. This is because space charge effects may be reduced by stretching the image in this plane.

While a device such as that shown in FIGS. 2 and 3 is operable, it involves moving parts which are generally to be avoided. In a preferred embodiment of the invention, such moving parts are avoided by adapting the principles of the induction motor so as to produce a rotating dipole field electrically with stationary coils.

Referring now to FIGS. 4, 5 and 6, the appropriate rotating field may be produced, by analogy to the induction motor, by a pair of windings each of which produces a uniform magnetic field, the two uniform magnetic fields being disposed at right angles to each other. If each of the two coils is excited by a sinusoidal input, and if the sinusoidal inputs are 90° out of phase with each other, a rotating magnetic field is produced. The windings may be identical except that they are arranged so that their configuration is displaced 90° with respect to each other. One of the windings is shown in FIGS. 4 and 5. As shown most clearly in FIG. 5, the turns of the winding therein shown are all directed into the paper in the left half of section A and in the right half of section B, and are directed out of the paper in the remaining portions. The result is to produce a south pole at section A and a north pole at section B so that the field pattern shown in FIG. 4 is produced. The simplest arrangement is of course to have a plurality of loops arranged as shown in FIG. 6. However, more sophisticated arrangements are of course possible in accordance with induction motor techniques and other well-known techniques. It can be shown that for the production of the uniform field the number of turns should vary sinusoidally as shown in FIG. 5.

The focusing effect of the deflector-focuser shown in FIGS. 4, 5 and 6 is quite similar to that of the rotating simple dipole of FIGS. 2 and 3, with β approximately equal to φ. However, there may be some modification of the simple pattern associated with FIGS. 2 and 3. For example, the field lines will bulge at the entrance and exit of the coil. This means that after being deflected through 30°, the effective value of β is somewhat less than φ.

While the foregoing description of the deflector-focuser shown in FIGS. 4, 5 and 6 refers to a two-phase arrangement, it is to be understood that three-phase circuitry (with 60° or 120° displacement as in a three-phase induction motor) and multi-phase arrangements are also comprehended within the scope of my invention.

Having thus described the principles of the invention together with illustrative embodiments thereof, it is to be understood that although specific terms are employed they are used in a generic and descriptive sense and not for purposes of limitation, the scope of the invention being set forth in the following claims.

I claim:

1. Deflector-focuser comprising means for producing a charged-particle beam along an axis and means for directing said beam onto a target lying in a planar section perpendicular to said axis and symmetrically disposed about said axis, said directing means comprising means for producing a magnetic field perpendicular to said axis adapted to deflect said beam through an angle φ in a trajectory having a radius of curvature R, said magnetic field havng an exit effective boundary whose normal is disposed at an angle β with respect to said beam after it leaves said magnetic field, whereby an azimuthal focusing action is produced, said magnetic field being so disposed that the focusing action for azimuthal focusing is as close to the target as possible, and means for rotating said uniform magnetic field about said axis.

2. Deflector-focuser according to claim 1, wherein said means for producing a mangetic field comprises a tube of magnetic material coaxial with said axis and a plurality of windings arranged in two groups on the inner surface of said tube, each group being so disposed and excited as to produce a magnetic field component transversely across said tube, the orientation of one said component being perpendicular to that of the other said component, the excitation of both said windings being sinusoidal but out of phase by $\pi/2$ radians.

3. Deflector-focuser according to claim 1, wherein said means for producing a mangetic field comprises a tube of magnetic material coaxial with said axis and a plurality of windings arranged in a plurality of groups on the inner surface of said tube, each group being so disposed and excited as to produce a magnetic field component transversely across said tube, the orientation of each said component being angularly displaced relative to the other said components, the excitation of said windings being sinusoidal but out of phase so as to produce a rotating field.

4. Deflector-focuser according to claim 1, wherein β = φ.

5. Deflector-focuser according to claim 1, wherein said magnetic field is substantially uniform.

6. Deflector-focuser according to claim 1, wherein said angle β is not less than φ/2.

* * * * *